United States Patent [19]

Sharkey et al.

[11] Patent Number: 5,545,171

[45] Date of Patent: Aug. 13, 1996

[54] ANASTOMOSIS CATHETER

[75] Inventors: Hugh R. Sharkey, Redwood City, Calif.; Benad Goldwasser, Tel Aviv, Israel; Stuart D. Edwards, Los Altos, Calif.

[73] Assignee: Vidamed, Inc., Menlo Park, Calif.

[21] Appl. No.: 310,684

[22] Filed: Sep. 22, 1994

[51] Int. Cl.$^6$ ................................................. A61B 17/04
[52] U.S. Cl. ........................................... 606/148; 606/139
[58] Field of Search .................................... 606/148, 139, 606/151; 623/1, 11, 12

[56] References Cited

U.S. PATENT DOCUMENTS

| | | | |
|---|---|---|---|
| 4,553,543 | 11/1985 | Amarasinghe | 606/148 |
| 4,577,631 | 3/1986 | Kreamer | 623/12 |
| 4,592,341 | 6/1986 | Omagari et al. | 623/12 |
| 4,787,899 | 11/1988 | Lazarus | 623/1 |
| 5,078,726 | 1/1992 | Kreamer | 623/12 |
| 5,207,695 | 5/1993 | Trout, III | 623/1 |
| 5,387,235 | 2/1995 | Chuter | 623/12 |

*Primary Examiner*—Gary Jackson
*Attorney, Agent, or Firm*—Haynes & Davis

[57] ABSTRACT

According to the present invention, an anastomosis catheter with internally mounted cam pieces holding a plurality of curved needles adjacent apertures in the side of the catheter is provided. The curved needles are attached to lengths of suture material which are installed to run along the outer surface of the central cam pieces to their distal end, where they reverse back along the inner core of the catheter. When the central cam pieces are withdrawn, and moved proximally, the cam surface forces the curved needles out the associated apertures. As the catheter is deployed in a hollow organ, such as a human urethra, the curved needles, as they are deployed, grasp the end of the urethra, which then can be held in position for suturing to the bladder. The other end of the suture materials could have straight needles attached to them to facilitate attaching the urethra to the bladder.

31 Claims, 8 Drawing Sheets

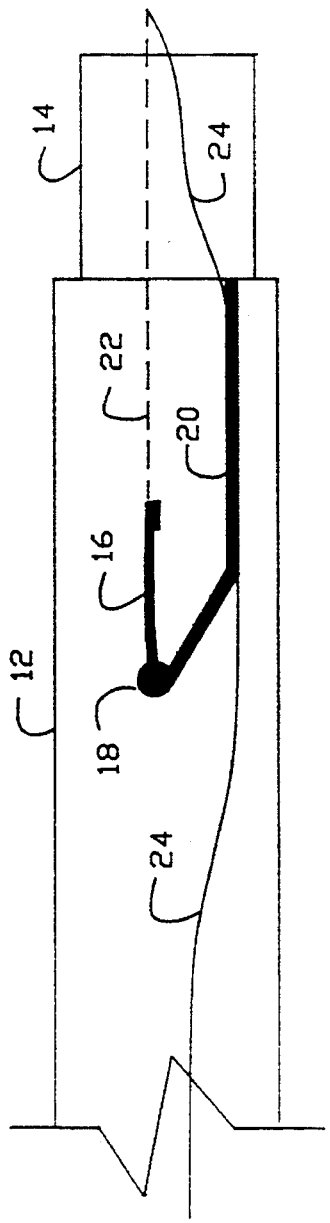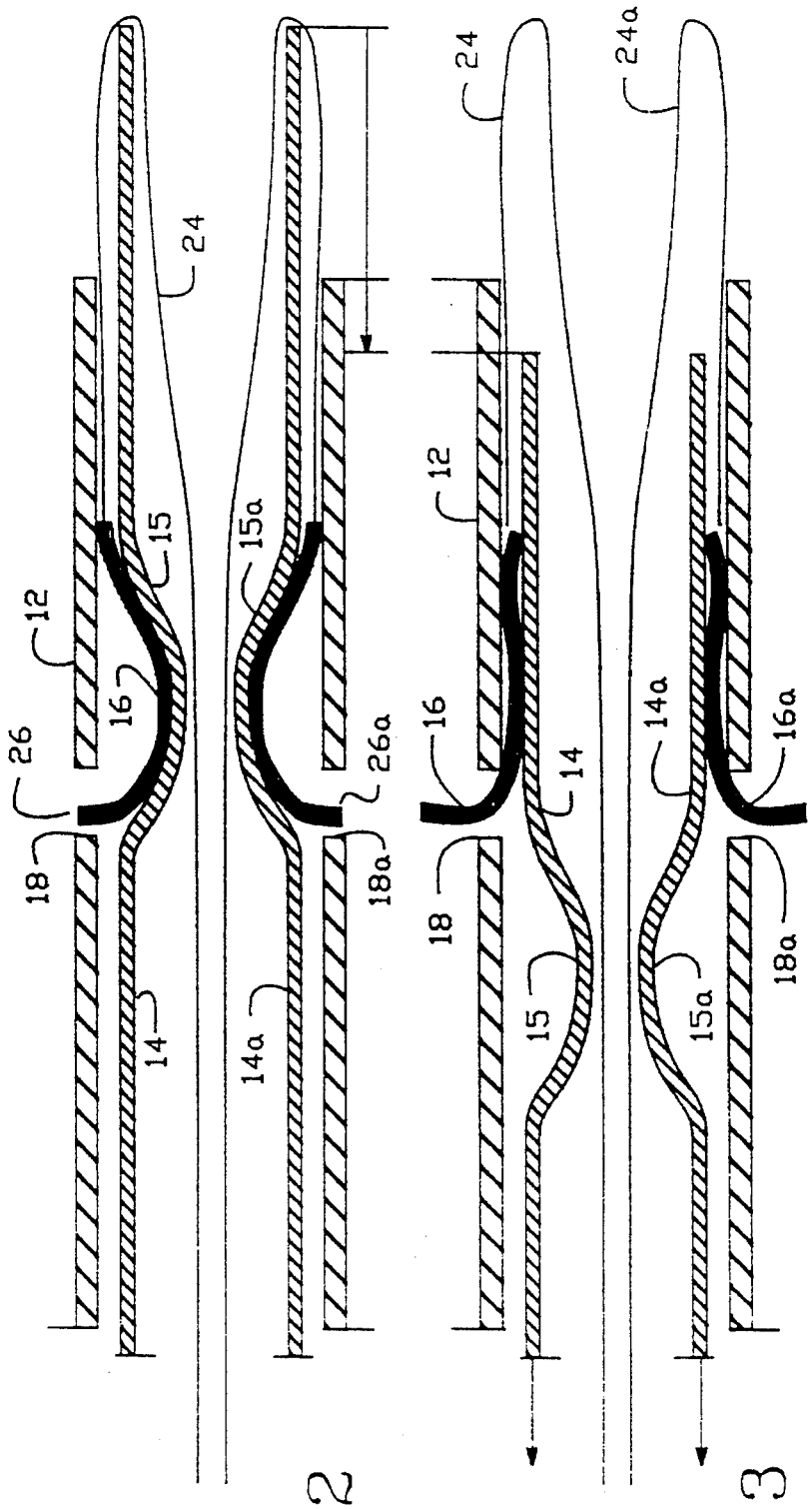
FIG. 1
FIG. 2
FIG. 3

ID CATHETER

FIELD OF THE INVENTION

This invention relates to an anastomosis catheter which is utilized for assisting in the joining together of two or more hollow body parts, and, more particularly, for example, for rejoining a transected urethra to the bladder after a radical prostatectomy.

BACKGROUND OF THE INVENTION

After certain operations are performed on a living body, and certain body parts been removed because of disease or other destruction of the organ, other body parts must be reconnected in order for the patient to survive and to maintain the remaining body functions. For example, in certain heart operations where bypass surgery is performed, sections of a person's coronary artery to the heart may either be completely replaced or actually bypassed during the heart bypass operation. While some of these arteries are large and are more easily manipulated by a surgeon, other arteries or hollow body organs are smaller and much more difficult to manipulate and hold in position while trying to join the ends thereof after a transectional operation.

In one instance, while a prostate gland is being removed in an operation called a prostatectomy, a section of the urethra is be removed when the prostate is removed, due to the occurrence of cancer in the prostate. After the operation to remove the prostate, the urethra must be reconnected to the bladder in order for the person to resume normal body functions, here, urination.

Heretofore, surgeons would grasp the end of a transected urethra, for example, and stretch it to the mating end of the urethra at the bladder perform delicate suturing operations with tiny, fine needles. Needless to say, some surgeons are very adept at this kind of anastomosis, but with radical prostatectomies becoming more common place, techniques for assisting in the rejoining of body parts, such as the urethra to the bladder, would be appreciated.

U.S. Pat. No. 4,553,543, to Amarasinghe, issued Nov. 19, 1985, reveals a plurality of flexible suture needles which are held in slots in a flared core by a sleeve which extends about the flexible suture needles and the core. The suture needles, and attached threads, are caused to penetrate the walls by a body duct, such as a blood vessel, by inserting the flared end of the core into the severed body duct and then forcing the needles to move longitudinally in the slots against the flared end of the core so that they bend outwardly and are driven through the wall of the duct. U.S. Pat. Nos. to Avant, 4,848,367, issued Jul. 18, 1989, 4,873,977, issued Oct. 17, 1989, and 5,047,039, issued Sep. 19, 1991, are all concerned with urethra and bladder anastomosis by varying techniques. Other U.S. Pat. Nos. to Tauber, 2,897,820; Demos, 4,784, 139; Roth, 4,911,164; Gottesman, 5,053,043; McKeating, 5,078,721; Jain, 5,080,664; Roth, 5,207,672; and Rothe 5,209,725 are all related to prior attempts at anastomosis and tissue ligation.

SUMMARY OF THE INVENTION

The present invention includes a medical probe device comprising a catheter having a plurality of needle apertures in a side thereof, with an associated suture needle positioned within the catheter adjacent each needle aperture. The needle apertures are adjacent the distal end of the catheter, the needles being deployed outward of said needle apertures upon activation thereof. One embodiment provides for cam sections within the hollow catheter for urging the suture needles out of the needle apertures upon activation of the deploying apparatus. The cam sections are positioned for longitudinal movement thereof within the catheter, each cam section having at least one cam surface. Each cam surface contacts the associated suture needle upon activation, the cam surfaces operating to urge the needles outward of the needle apertures upon longitudinal movement of the cam sections.

Each suture needle can be curved such that the curve approximates that of the cam surface of the cam sections, with the needle riding in the space defined by the cam surface prior to activation of said deployment apparatus, with the needle riding up on said cam surface and outward of said needle aperture upon the longitudinal movement of the cam sections. Each suture needle has a distal end and a proximal end, with the distal end having a sharp tip which is moved outward of the associated needle aperture, with its proximal end being attached to suture material or thread. The medical probe device further includes a plurality of slots in the side of the catheter running from each needle aperture to the proximal end of the catheter, the slots allowing the removal of the suture material from the catheter subsequent to deployment of each suture needle. Each suture needle is positioned within the catheter with the proximal end of the suture needle facing toward the distal end of the catheter. The suture material is attached to the needle being positioned longitudinally forward within the catheter toward the distal end thereof and around said cam sections and back through the center section of said catheter toward the proximal end of the catheter, wherein a loop of suture material remains beyond the distal end of the catheter subsequent to the deployment of each suture needle.

The medical probe device may further include a second suture needle attached to the other end of the suture material, wherein the suture material and the second needle is removable from the catheter via the slots in the side of the catheter. Depending on the internal construction of the catheter, the suture needles may be deployed upon distal movement of the cam sections within the catheter, or, alternatively, by the proximal movement of said cam sections.

Another embodiment for the medical probe device herein discloses a hollow catheter having a plurality of needle apertures in the side thereof for directing a plurality of suture needles outward through said needle apertures and through adjacent tissue, with a suture needle positioned in all or most of said apertures, and including apparatus for deploying the suture needles outward through the apertures. The deploying apparatus includes a wedge segment cylinder within the catheter which comprises a plurality of wedge segments for urging the suture needles out of the needle apertures upon activation of said deployment apparatus. Each of the wedge segments comprises cam segment and cam section combinations which are generally of complementary cam shapes such that in one position each cam segment and cam section are substantially in a mating configuration. The cam segments are positioned for longitudinal movement thereof in the catheter, each of said cam segments having at least one cam surface, wherein the cam surfaces of the cam segments contact the suture needles upon activation, the cam surfaces operating to urge the suture needles outward of said needle apertures upon longitudinal movement of the cam segments.

In this embodiment, the suture needles are curved such that the curve approximates that of the cam surface of the cam segments, the needles riding in the space defined by the space between the cam segments and the cam sections prior to activation of the deployment apparatus, the needles riding up on said cam surface and outward of said needle apertures upon the longitudinal movement of the cam segments. Each of the suture needles has a distal end and a proximal end, the distal end having a sharp tip to be moved outward of each needle aperture, with the proximal end being attached to suture material. The medical probe device further includes a plurality of slots in the side of the catheter running from the needle apertures to the proximal end of the catheter, the slots allowing the removal of the suture material from the catheter subsequent to deployment of the suture needles.

The wedge segments can be selectively activated to individually deploy the suture needles, the suture needles being positioned within the catheter with the proximal ends of the suture needles facing toward the distal end of the catheter. The suture material attached to each of the suture needles is positioned longitudinally forward within the catheter toward the distal end thereof and around the wedge segments and back through the center section of the catheter toward the proximal end thereof, wherein a loop of the suture material remains beyond the distal end of the catheter subsequent to the deployment of the suture needles.

This embodiment also includes a plurality of second suture needles attached to the other end of each of the suture material, wherein the suture material and the second needles are removable from the catheter via said slots. Additionally, the cam sections are fixedly attached within said catheter. Depending on the internal configuration of the catheter, the suture needles are deployed upon distal movement of the cam segments within the catheter, or can be deployed upon proximal movement of the cam segments within the catheter.

DESCRIPTION OF THE DRAWINGS

For a more complete understanding of the invention, reference may be had to the following detailed description of the invention in conjunction with the drawings wherein:

FIG. 1 is a top view of a first version of the distal end of a catheter in accordance with the principles of the present invention;

FIG. 2 is a side, sectional-view of the distal end of a catheter showing the suture needles prior to deployment;

FIG. 3 is a side, sectional-view of the distal end of a catheter in accordance with the principles of the present invention showing the suture needles after deployment;

FIG. 7a is a side view of a wedge section utilized in FIG. 5; while

FIG. 8a is a bottom view of the wedge shown in FIG. 7; while

FIG. 12a is an enlarged cross-sectional side view of the embodiment shown in FIG. 4 showing the wedge section cylinder within the confines of the catheter illustrating the placement of the suture needles and suture material; while

DETAILED DESCRIPTION OF THE INVENTION

Figure 4:
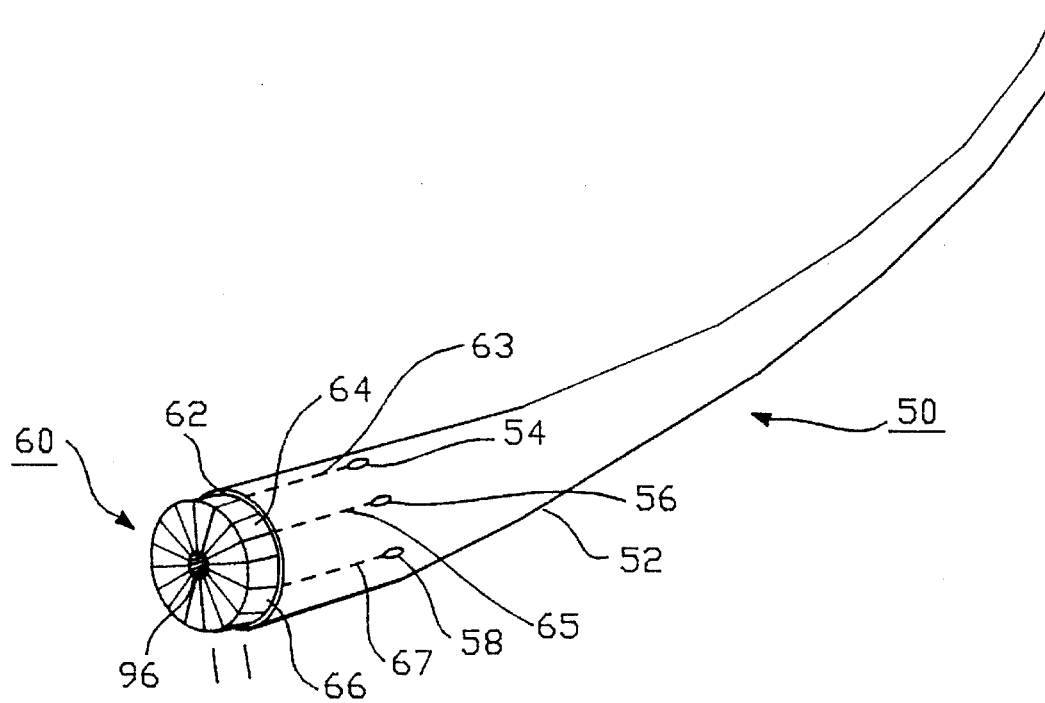
FIG. 4 is a perspective view of the distal end of a catheter showing a second version of the present invention prior to needle deployment.

FIG. 1 of the present invention is a side view of the distal end of a catheter utilizing the principles of the present invention. The distal end of catheter 12 is shown which could comprise a cylindrical or other generally round tubular device made of surgical stainless steel or other appropriate material. Adjacent the end of catheter 12 would be an aperture, or hole 18, together with a slot 20 running at an angle from aperture 18 and then longitudinally along the length of the catheter to the distal end thereof. Needle 16 is, in this figure, totally within the confines, or central core, of the hollow catheter 12. One end of suture needle 16 is connected to suture material 22, which is shown in dashed lines in FIG. 1, as the suture material is not seen in this figure as it is within the confines of the catheter 12 and cam section 14. The other end of the suture 24, as it exits the central core of the cam section 14 and catheter 12, is seen as having been removed from the catheter by means of aperture 18 and slot 20. The other end of suture material 24 could be a straight needle which could be pulled out, and in this figure has already been pulled out, to utilize it in suturing the bladder to the urethra, for example. Once the suture has been made, the surgeon can continue to suture as desired utilizing the curved suture needle 16, and then tie off the suture in the normal course of the operation.

FIG. 2 is a side-sectional view of catheter 12 prior to deployment of the needles 16 and 16a. Cam sections 14 and 14a are in position with the distal ends of the cam sections protruding out beyond the distal end of the catheter 12. The catheter could be deployed, or inserted, in a hollow body organ such as the male urethra with the cam sections 14 and 14a in this position shown in FIG. 2, or the cam sections could have been installed in the catheter 12 with the cam sections further located proximally of the distal end of catheter 12 so that the distal end of cam sections 14 and 14a could be adjacent to or behind, or within the central core of the catheter 12. That is, if the cam section 14 is moved to the right before deployment as shown in FIG. 2, then the curved needle 16 will move along the inside edge of catheter 12 until the end 26 of needle 16 reaches aperture 18 where it will, due to the slight bias in the curved needle 16, snap into aperture 18 as shown in FIG. 2. Similarly, if cam section 14a had been further to the left in FIG. 2, upon deployment of cam section 14a to the right in FIG. 2, the needle 16a will snap into the aperture 18a, as shown in FIG. 2. Cam sections 15 and 15a on cam sections 14 and 14a enclose the curved needles, having the approximate shape thereof, prior to positioning as shown in FIG. 2. Cam sections 14 and 14a can be separate articles, separately activatable, on one tubular structure fitting inside catheter 12.

FIG. 3 shows the apparatus of FIG. 2 with the cam sections 15a and 15b retracted within the inner core of catheter 12. When the cam sections 14 and 14a are withdrawn from the distal end toward the proximal of the catheter 12, the cam sections 15 and 15a exert pressure on curved needle 16 and 16a during the cam movements to the left and further force the curved needle 16 and 16a out through apertures 18 and 18a, as seen in FIG. 3. When the cams 15a and 15b are retracted, or withdrawn, from within the core of catheter 12, loops 24 and 24a of suture material are left protruding beyond the distal end of the catheter 12. This loop of catheter material 24 and 24a allows the operating surgeon to grasp the suture needle with a forceps device to withdraw the other end of the suture material out from within the central core of the catheter 12 for use in suturing the other organ to the present organ, such as, for example, a bladder to a transected urethra.

FIG. 4 is a three dimensional, perspective view of a second embodiment of the present invention. The anastomosis catheter 50 of this embodiment includes a catheter tube 52 which, again, could be surgical stainless steel. Adjacent the distal end of the catheter 52 are placed a series of apertures, 54, 56, 58, annularly around the circumference of the catheter 52. Three apertures are shown in FIG. 4; however, more apertures may be utilized with a possibility of eight or more being included. Wedge segment cylinder 60 extends out from the distal end of the catheter 52 a short distance. As only three apertures are shown, the description will include only wedge segments 62, 64, and 66, but an examination of FIG. 4 will reveal a total of eight wedge segments, which will be operational for five additional apertures not seen in FIG. 4. Wedge segment cylinder 60 comprises eight wedge segments comprising the cylinder constructed such that there is a central hole which runs axially along the wedge segment cylinder within the central core of catheter 52. Seen also in FIG. 4 are eight suture materials which would be combined with the appropriate needle arrangement, not seen, in conjunction with the respective apertures. Thus, in FIG. 4, wedge segment 62, suture 63, and aperture 54 are in operational relationship; while wedge segment 64, suture 65, and aperture 56 are in operational relationship; and wedge segment 66, suture 67, and aperture 58 being in operational relationship together.

Figure 5:
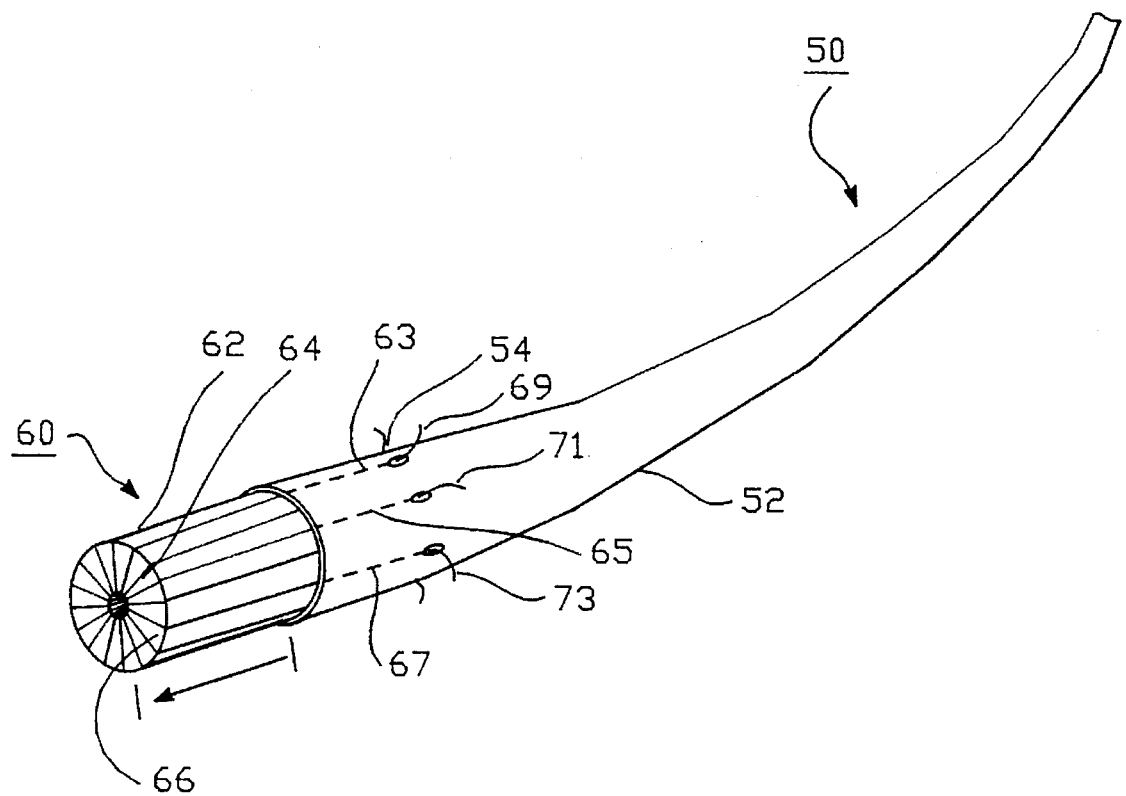
FIG. 5 is a perspective view of the embodiment of FIG. 4 after needle deployment.

In FIG. 5, the wedge segment cylinder 60 is shown to have been extended further out from catheter 52. In FIG. 5, all of the wedge segments have been deployed; however, each of the wedge segments can be operated individually, sequentially, or all together. As the wedge segment cylinder 60 is advanced in the distal direction in catheter 52, the suture material which is held taut over the ends of the wedge segments, pulls the curved needles which are attached to the end of each suture material. Thus, as each needle reaches it associated aperture, it is forced out of the aperture in the manner hereinafter described. Thus, as wedge 62 is advanced distally, suture material 63 is pulled along with it and when needle 69 reaches aperture 54, needle 69 is forced out of aperture 54 into its deployed position. Similarly, wedge segments 64 and 66 operate on suture material 65 and 67 to deploy needles 71 and 73 out of apertures 56 and 58, as seen in FIG. 5. The suture material, as described herein, could be typical suture thread material such as catgut, silk, cotton, nylon or other material but if the sutures are meant to be left in place within a living body, the suture material should be of the type that is absorbed by the body after the joining of the transected organs.

Figure 6:
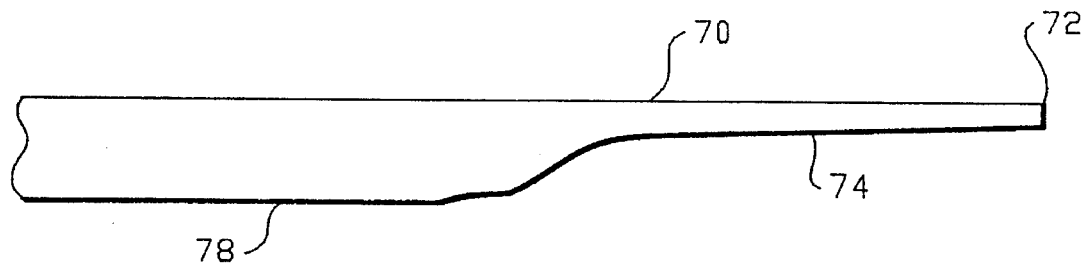
FIG. 6 is the side view of a cam which is one part of a section of the embodiment FIG. 5.

FIGS. 6 through 10 are side section views of the wedge segments and cam devices for the embodiments shown in FIGS. 4 and 5. FIG. 6, for example, depicts a cam section which is an elongated structure which tapers back from a leading thin edge thereof to a place adjacent the distal end thereof where the thin taper expands to a wide dimension to form a shoulder or a cam surface 76 seen in FIG. 6. That is, cam 70 has an elongated section culminating in distal front end 72 which tapers back along the surface 74 to reach a shoulder 76 which then becomes a wider section 78.

Figure 7A:
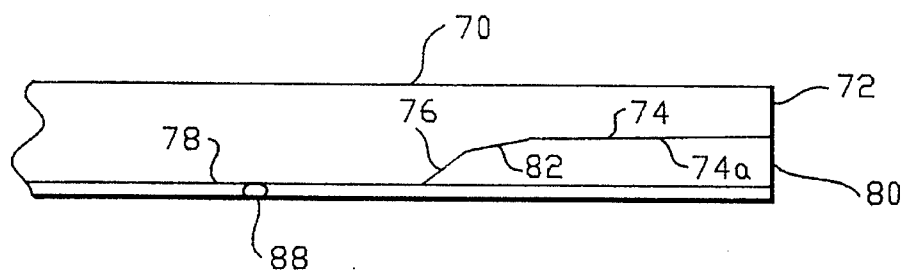

FIG. 7a is a side sectional view of the wedge segment 70 together with complementary designed cam follower 80. That is, cam section 70 is wedge shaped and includes the front section 72 which tapers back at area 74 to a rounder section 76 to the remaining part of the shaft at 78. Cam section 80 includes the shape complementary to the cam 70. That is, cam section 80 includes a section 74a which is complementary to the shape 74 of the cam 70. Moving away from the distal end thereof, shape 74 reaches a point where a rounder section 82 mates exactly with shape 76 of cam 70. The front view of the wedge segment is shown in FIG. 70b. Wedge segment 84 includes the cam segment 70 and the cam section 80. Together they form wedge segment 84 which could be one of the wedge segments seen in FIGS. 4 and 5.

Figure 7B:
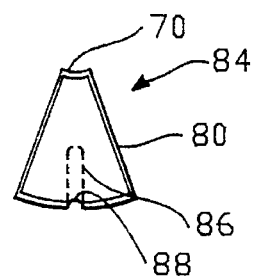
FIG. 7b is a view from the distal end thereof.
Figure 8A:
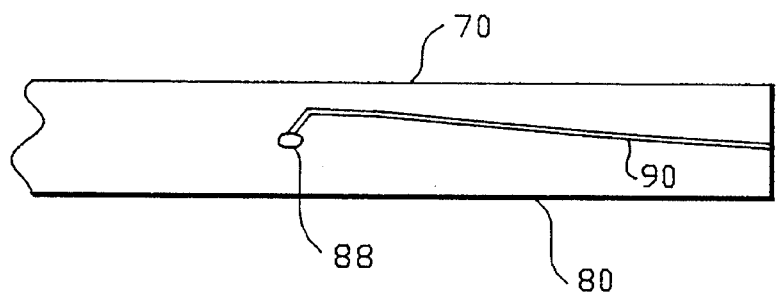
Figure 8B:
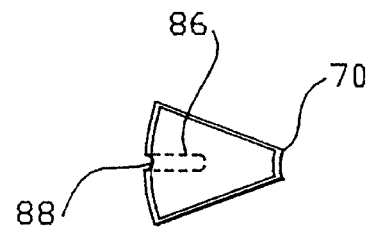
FIG. 8b is a view from the distal end thereof.
Figure 9:
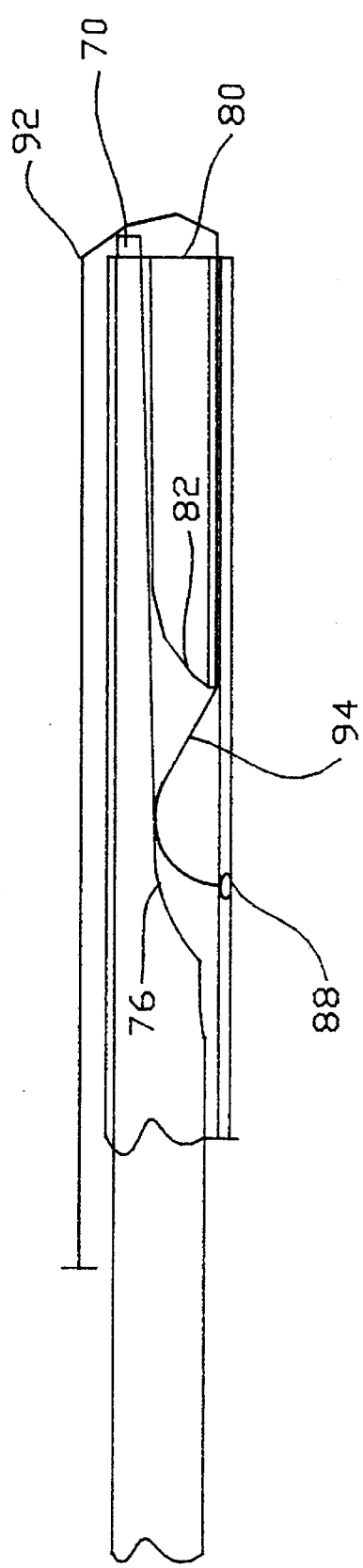
FIG. 9 is a side-sectional view of the cam in FIG. 6 and the wedge in FIG. 7 prior to deployment of the suture needle.

FIG. 8a is a bottom view of the same wedge segment seen in FIG. 7a and FIG. 7b. Seen on the bottom of FIG. 8a is the aperture 88 from which the curved needle will emanate upon deployment. Slot 90 is provided to allow the removal of the needle and the suture material without having to pull it through the entire mechanism. FIG. 8b is the same as FIG. 7b but is oriented to show the relative position and configuration of the cam segment 70 and the cam section 80. FIG. 9 is a side-sectional view of the apparatus shown in FIGS. 6 to 8, but now in working relationship together with a needle and suture material. Cam segment 70 is shown in its undeployed state away from its mating position with cam section 80. Positioned in the space between the cam surface 76 of cam 70 and cam surface 82 of cam section 80 is the curved needle arrangement 94. Attached to the inner end of curved needle 94 is a suture material 92 which is seen to run forward toward the distal end of the catheter and then around the front thereof and back along the cam segment 70 which is the hole 96 seen in FIG. 4.

Figure 10:
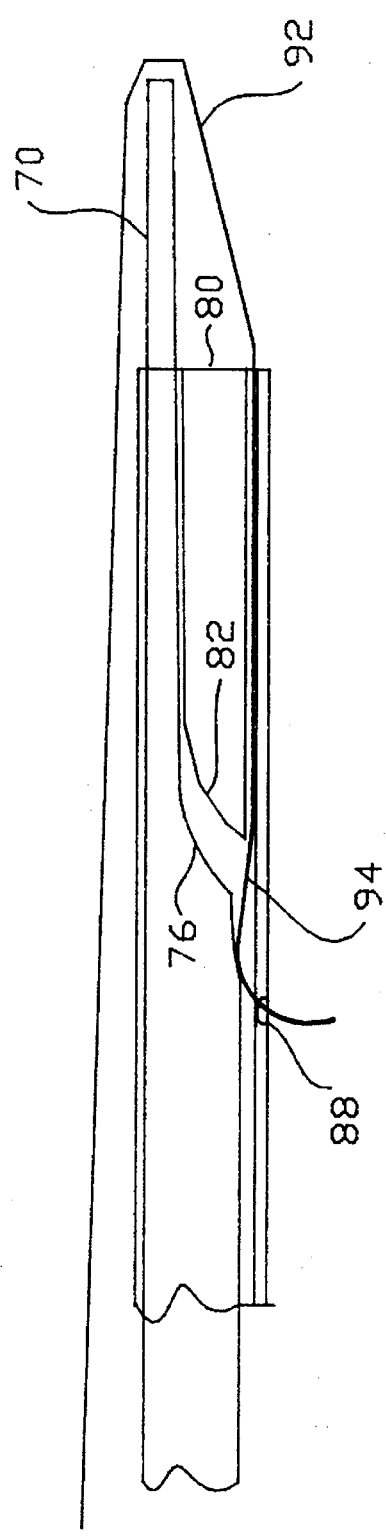
FIG. 10 is a side-sectional view of the embodiment shown in FIG. 9 subsequent to the deployment of the suture needle and displacement of the suture material.

FIG. 10 is a side view of the same arrangement seen in FIG. 9 with, however, the cam section 70 moved distally along the core of the catheter until the cam surface 76 comes in contact with curved needle 94 which, upon movement of the cam 70 to the distal end, or right side of FIG. 10, forces the curved needle 94 out aperture 88 with the curved needle operating as a cam follower in this instance. At the same time, the cam surface 76 is forcing the curved needle 94 out of aperture 88, the distal end of cam segment 70 is forcing additional suture material out the front of the catheter which, as set forth above, allows an operating surgeon to grasp the suture material with a forceps or other grasping device to pull the suture material out from the central core of the catheter. As set forth above, the other end of the suture material from the curved needle 94 could have a straight needle attached to it to facilitate the suturing of the bladder to the transected end of the urethra, for example.

Figure 11A:
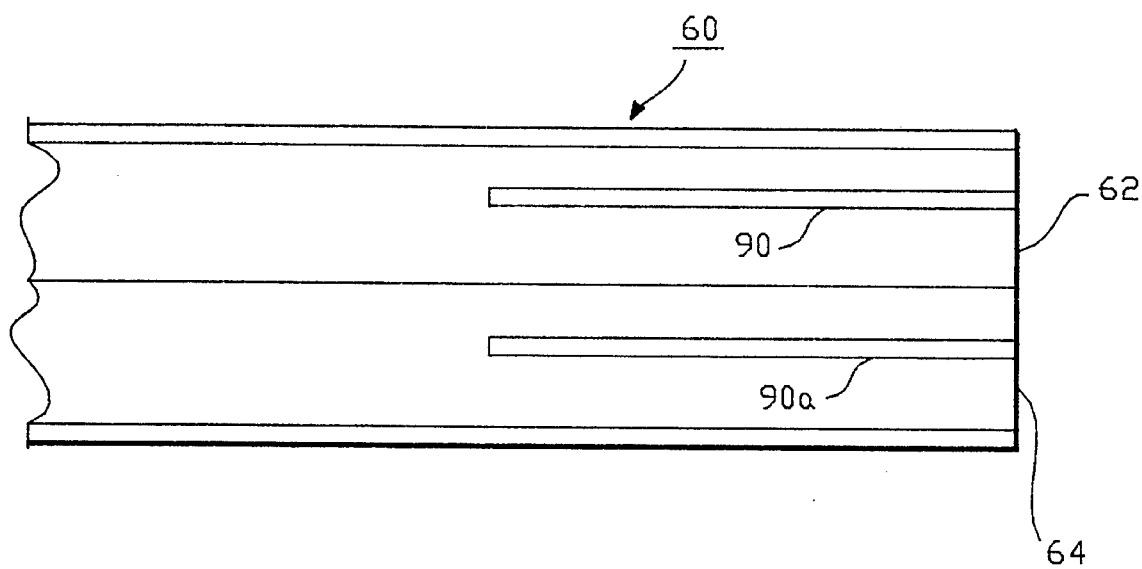
FIG. 11a is an enlarged view of the wedge section cylinder of the embodiment of FIG. 4; while FIG. 11 b is a distal end view thereof.
Figure 11B:
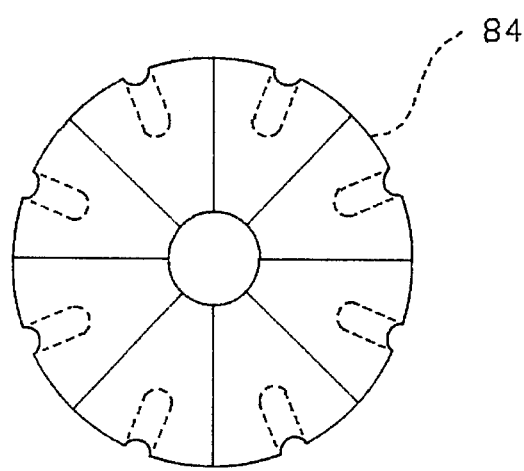

FIG. 11a is a side view of the wedge section cylinder 60 seen in conjunction with FIGS. 4 and 5. The side view 11a of the wedge section cylinder 60 comprises wedge segments 62 and 64 as seen in FIGS. 4 and 5. Shown in representative form are slots 90 and 90a for wedge section segments 62 and 64. FIG. 11b is a view from the distal end of wedge section cylinder 60 including eight such wedge segments 84 which are the type shown and described in conjunction with FIGS. 6 to 10.

Figure 12A:
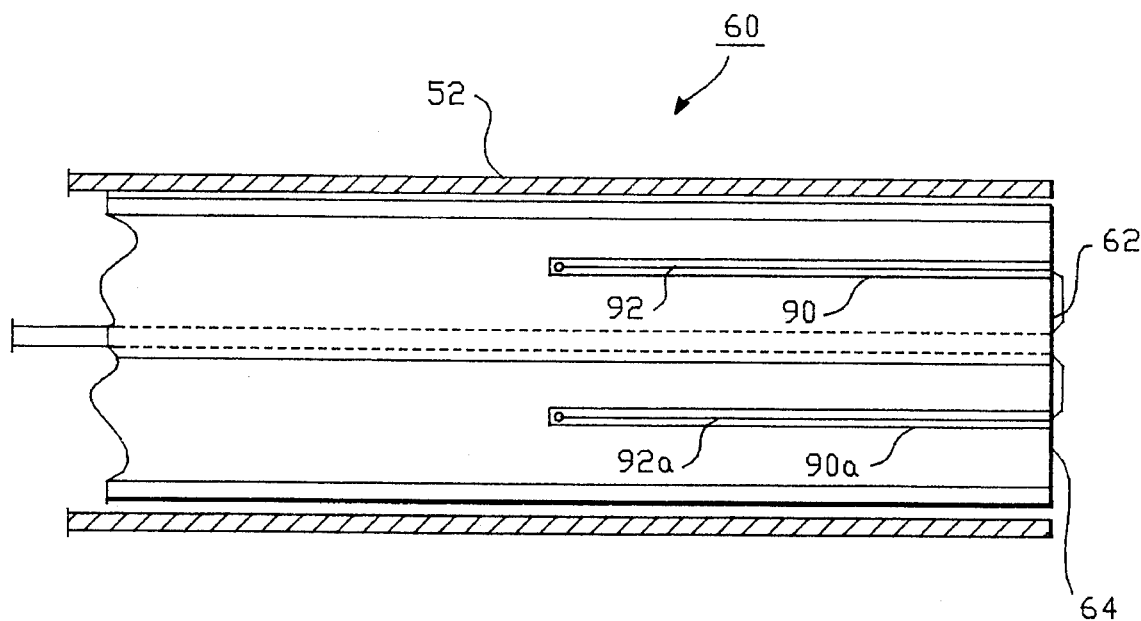
Figures 12B, 12C:
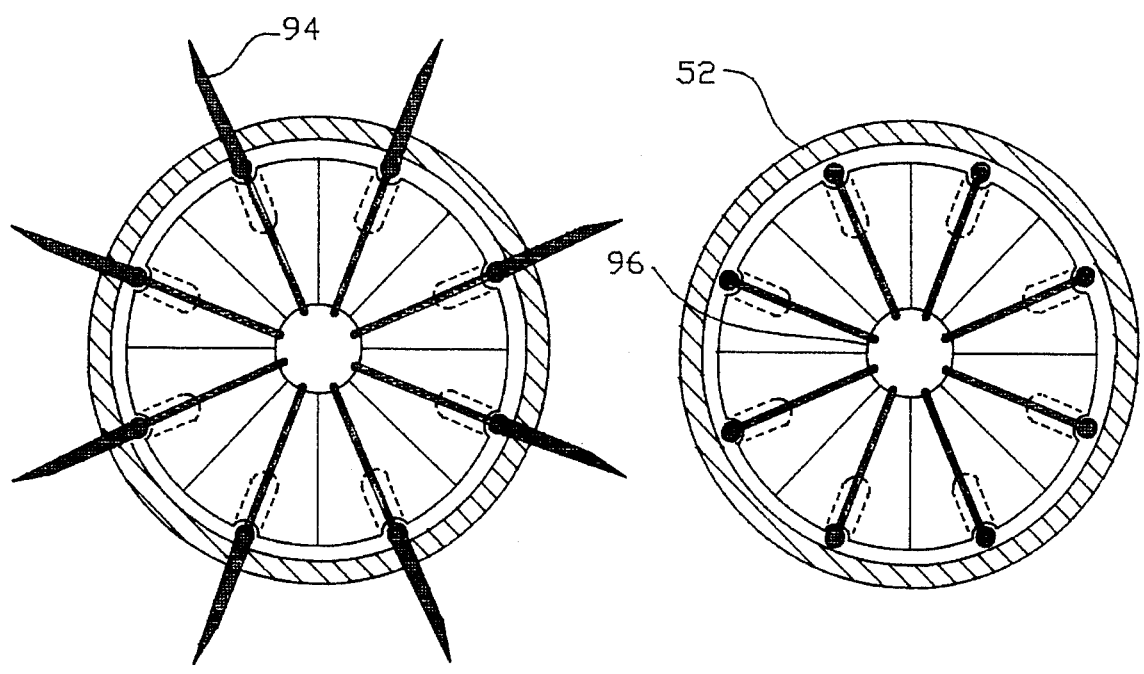
FIG. 12b is a distal end view thereof prior to suture needle deployment.
FIG. 12c is a distal end view thereof with the suture needles deployed.

FIG. 12a is a cross-sectional view similar to that of FIG. 11a, but FIG. 12a includes a side view of the catheter 52 so that the relative placement of the wedge section cylinder 60 can be seen in relation to the catheter 52. Positioned in grooves 90 and 90a are the suture material 92 and 92a which are seen to run in the grooves 90 and 90a which are similar to the groove seen in conjunction with FIG. 8a. The suture material 92 runs along the bottom edge of each wedge section and across the front or distal end of the wedge section cylinder 60 and then back along the center opening 96. In FIGS. 12a and 12b are eight such wedge segments which could be in less number or greater number, but, for convenience, eight are shown in FIG. 12b. FIG. 12c is a figure similar to FIG. 12b; however, the curved needles have been deployed out of each representative or associated aperture hole in order to deploy the curved needles into the urethra as is desired.

In operation, an operating surgeon would manipulate slide sections as desired to move each cam segment into position. As each cam segment is in position, each associated curved needle is deployed out the associated aperture holes into the inner wall and out the outer wall of the body tube, here, for example, a urethra. In this manner, the urethra can be positioned adjacent the complementary tube emanating from the bladder, while the catheter invention as disclosed allows for accurate placement and removal of the center suture material lengths which are or may be attached to straight needles mounted on the inner core of the catheter arrangement. That is, at the desire of the operating surgeon, each curved needle would be deployed to grasp the inner surface of the urethra. As described above, this allows a section of the suture material to be grasped by a forceps or other device by the operating surgeon who can then remove the straight needle from the center core of the catheter. These straight needle segments can be used to begin the suturing action for each of the curved needles at the other ends of the suture material to sew the transected ends of the male urethra and battery together to allow the mating of these transected ends to be joined in a permanent manner.

Figure 13:
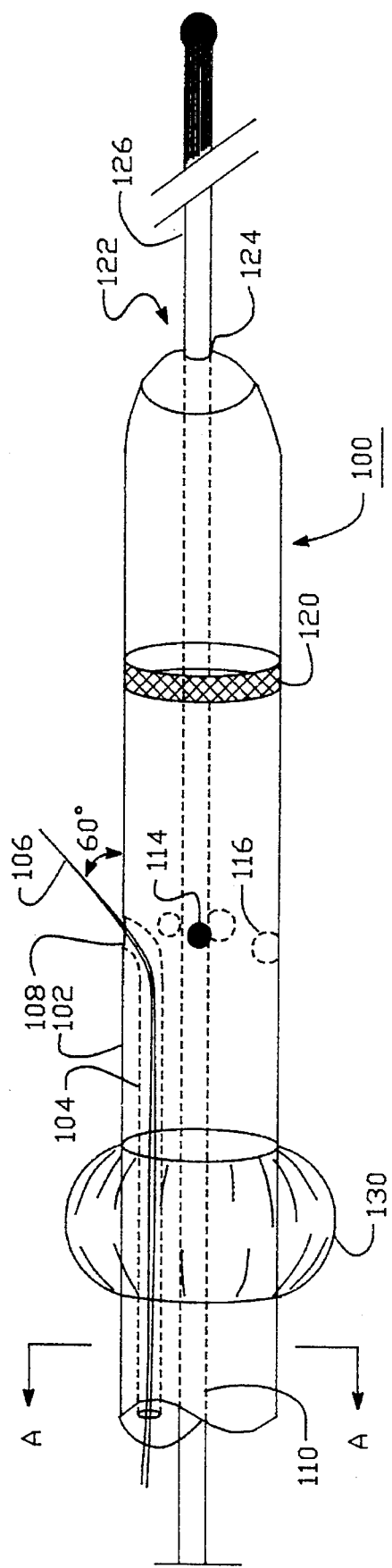
FIG. 13 is a side view of a third embodiment of the present invention showing the annular balloon, deployed needles and grasping handle.

FIG. 13 is a three dimensional isometric view of still another embodiment of the present invention. Catheter 100 includes an elongated cylindrical body 102 which has several axial lumens built therein. Catheter 100 further includes a central lumen which is longitudinaly extended. It can be made of plastic or surgical steel. Axial lumen 104 is parallel to the axis of the catheter 100, but near the distal end of the catheter it makes a sharp turn to the outer surface of the catheter terminating at aperture 108. In lumen 104, and exiting at aperture 108 is suture material or thread 106 which has a sharpened end to allow for penetration of body tissue or it could comprise a suture with a sharpened needle to effect the same result. The suture could be made of any appropriate suture material, such as vicryl or surgical gut. The suture material with the sharpened end 106 exits the catheter at aperture 108 at approximately a 60 degree angle due to the curve of the lumen 104 as it approaches aperture 108. The angle at which the suture material exits the catheter 100 can be adjusted by the severity of the angle at which the lumen approaches aperture 108. A similar lumen would be associated with aperture 114 as well as a similar suture material for aperture 116. However, to simplify FIG. 13, the sutures are not seen to emanate from apertures 114 or 116. Annularly around the distal end of the catheter is a marker band 120. This marker band could either be compressed into the surface of the catheter or could be a different material such as a painted surface to mark this position. The marker band 120 is approximately 3 mm back from the distal end 122 of the catheter 100. The marker band could be about 1 millimeter forward of the apertures 108, 114, and 116, which themselves are approximately 1½ cm in front of an annular elastic balloon 130. This balloon is mounted on the outside surface of the catheter 100 and inflated by a lumen more clearly seen below in conjunction with FIG. 18. At the distal end 122 of catheter 100 is the opening 124 of a lumen 110 which includes a traction handle 126 that is moveable in the longitudinal axial direction into and out of catheter 100. This traction handle would be approximately eight inches long as it extends out of the distal end of catheter 100.

Figure 14:
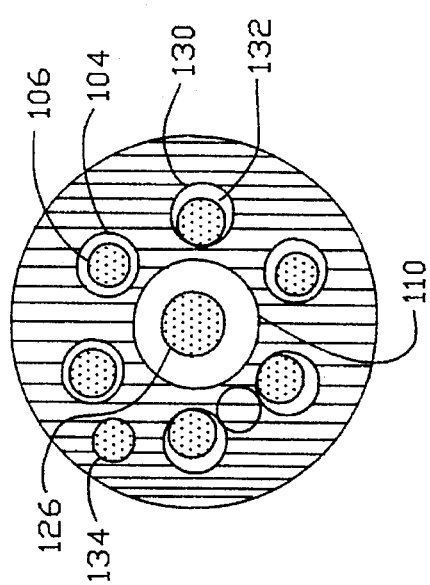
FIG. 14 is a view of section A—A of the handle seen in FIG. 13.

FIG. 14 is a cross-sectional view of the catheter as seen at section A—A of FIG. 13. Six lumens are shown in the cross section which carry the sutures seen and described in FIG. 13. That is, lumen 104 in FIG. 14 is the same as lumen 104 in FIG. 13 and carries suture 106 inside lumen 104. Similarly, lumen 131 carries suture 132, and in a similar manner the other four lumens would similarly carry associated sutures. Also in FIG. 14 is central lumen 110, which is also seen in FIG. 13, and carries within it the traction handle 126. Traction handle 126 is preferably made of plastic and runs through the center of catheter 100. It is capable of longitudinal movement. It is a long narrow rod with a round end 127. It enables the present invention to stretch the urethra to bring it into close proximity of the bladder. This is done by extending traction handle 126 toward the top of the page. In this process, round 127 stretches the urethra. Once the urethra is positioned in close proximity of the bladder, catheter 100 can be used to sew the two parts together. At the bottom of FIG. 14 is lumen 134 which would carry the balloon inflation and deflation material, which could be air, but more likely a modified saline solution. Balloon 130 could be made of any elastic materials such as vicryl, silicon or latex. It is attached to the outer surface of catheter 100 using different techniques. For example, if balloon 130 is made of silicon, adhesive material could be used to attach it to catheter 100. On the other hand, if latex is used to make balloon 130, known mechanical bonding methods could be used to attach it to catheter 100.

Figure 15:
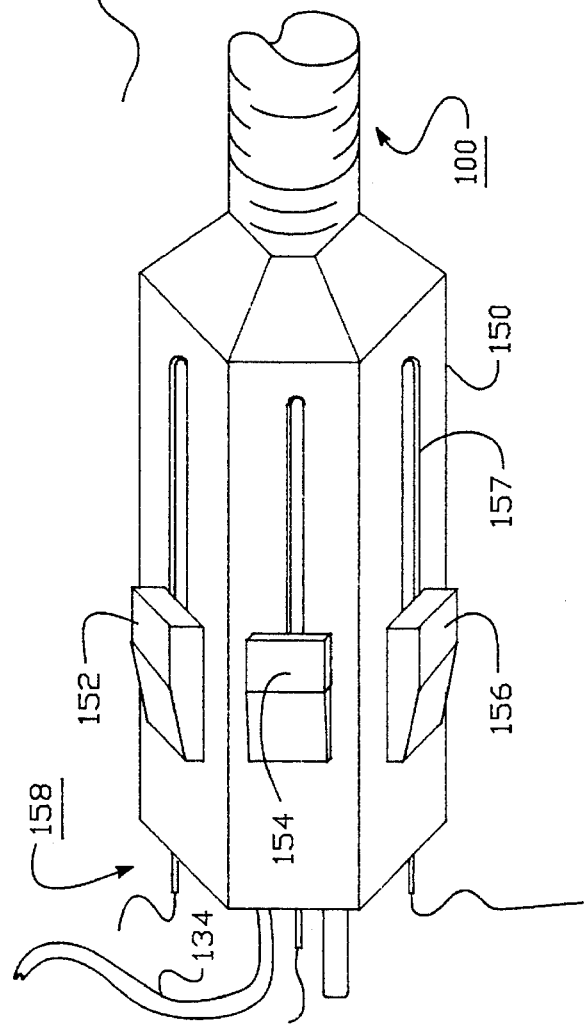
FIG. 15 is a three dimensional side view of the handle portion of the catheter of this embodiment showing the deployment sliders for each of the suture needles.

FIG. 15 is a three dimensional side view of the handle 150 of the catheter of the present invention. Section 150 of the catheter 1 00 includes three deployment sliders 152, 154, and 156 which are connected inside the handle arrangement 150 to a suture material as seen in FIG. 13. However, inasmuch as the suture material is more easily pulled than pushed, the traction handle 126 would be more likely utilized to pull each of the deployment sliders which would deploy each of the suture ends 106 into the urethra, in this example. Deployment sliders 152, 154, and 156 would be utilized to withdraw toward the proximal end 158 of handle 150 each of the suture material filaments upon completion of the attachment of the urethra to the bladder.

Figure 16:
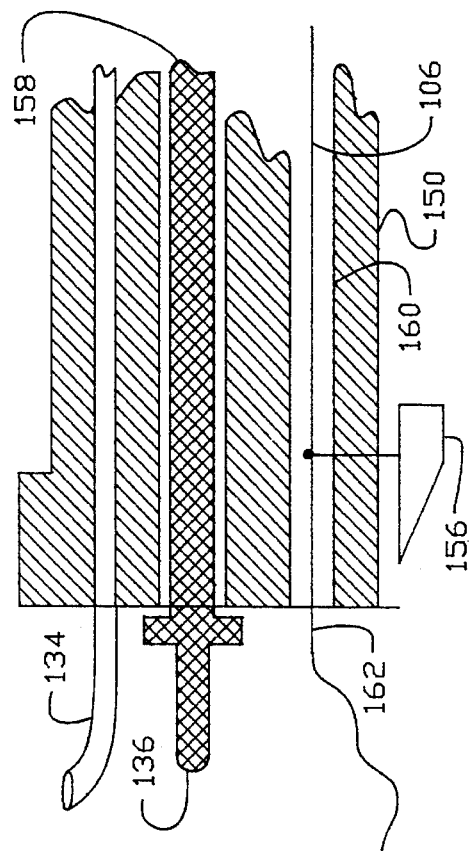
FIG. 16 is a cross-sectional side view of the embodiment shown in FIG. 15.

FIG. 16 is a side view of handle 150 seen and described in conjunction with FIG. 15. Balloon inflation lumen 134 is formed in the handle which is connected to an external source of fluid for inflation thereof. The proximal end 136 of the traction handle 126 is shown in its lumen 138; while lumen 160 is shown to include the proximal end 162 of a suture material 106. Handle 156 is seen to be attached to suture 106 in a guide path not seen in FIG. 16 but clearly shown as slide path 157 in FIG. 15.

Figure 17:
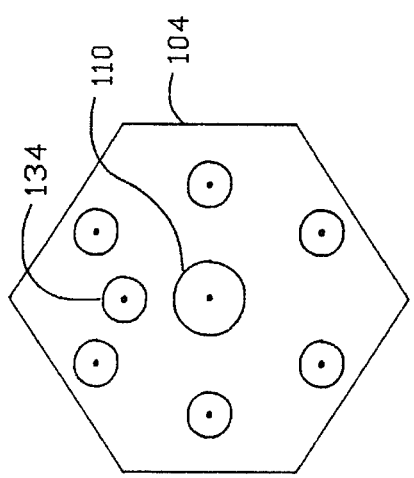
FIG. 17 is a proximal end view of the embodiment shown in FIG. 15.

FIG. 17 is an end view of the handle shown and described in conjunction with FIG. 15. Lumen 110 is shown which would house the traction handle 136; while lumen 104 and the other five lumens are shown as suture delivery lumens in FIG. 17. Also included is the balloon inflation lumen 134.

In operation, the catheter 100 would be inserted into the patient's urethra and passed in the urethra until the transected end of the urethra is at the marker band 120 as seen in FIG. 13. The distal end of catheter 100 would be protruding beyond the end of the transected urethra. Upon selective actuation of deployment sliders 152 and any of the other deployment sliders, the sharpened ends of sutures 106 would be deployed into the end of the urethra by the operating surgeon. By utilizing needle forceps, each of the sutures can be pulled out of the catheter for use in suturing the urethra to the complementary end thereof on the bladder of the patient. Alternatively, the traction handle may be grasped by the surgeon which will deploy all of the sharp sutures into the urethra at one time. After the urethra has been re-attached to the bladder, the deployment handles can be moved rearwardly to the proximal end of the handle 150 which will withdraw the sutures material subsequent to cutting thereof by the operating surgeon. Then the entire catheter can be slowly removed from the urethra after deflation of the balloon 130. This leaves the urethra attached to the bladder, having been accurately positioned thereto and sutured by the operating surgeon.

Shown in these latter figures are, in cross-section, six lumens carrying sutures while on the side views there are shown three apertures containing sutures. However, the invention is not limited to six but could include more apertures with sharpened sutures in accordance with the principles of the present invention.

As mentioned above, the device of the present invention can be used where there is a need to reattach two tubes with the body. In addition to the situation where the urethra must be connected to the bladder, the present invention can be used to connect the bottom end of the colon to the anus after the rectum is removed to cure colon cancer.

While the invention has been described with reference to specific preferred embodiments, it will be understood by those skilled in the art that various changes may be made and equivalents may be substituted for elements thereof without departing from the true spirit and scope of the invention. In addition, many modifications may be made without departing from the essential teachings of the invention.

What is claimed is:

1. A medical probe device comprising;
   a hollow catheter including at least one needle aperture in a side thereof for directing a suture needle outward through at least said one needle aperture and through adjacent tissue;
   a suture needle positioned in at least one of said apertures;
   a deployment apparatus for deploying said at least one suture needle outward through at least one of said apertures, said deployment apparatus including a cam section device, said cam section device positioned in said hollow catheter to permit longitudinal movement of said cam section device in said hollow catheter, said cam device including a cam surface, wherein said cam surface of said cam section device contacts said suture needle upon activation, said cam surface operating to urge said needle outward of said needle aperture upon longitudinal movement of said cam section device.

2. The medical probe device of claim 1 wherein said suture needle is curved such that said curve approximates that of said cam surface of said cam section device, said needle riding in the space defined by said cam surface prior to activation of said deployment apparatus, and said needle riding up on said cam surface and outward of said needle aperture upon said longitudinal movement of said cam section device.

3. The medical probe device of claim 2 wherein said suture needle has a distal end and a proximal end, said distal end having a sharp tip and moved outward of said needle aperture, and said proximal end being attached to suture material.

4. The medical probe device of claim 3 further including a slot in said side of said catheter running from said needle aperture to the distal end of said catheter, said slot allowing the removal of said suture material from said catheter subsequent to deployment of said suture needle.

5. The medical probe device of claim 4, wherein said suture needle is positioned within said catheter with the proximal end of said suture needle facing toward the distal end of said catheter, the suture material attached to said needle being positioned longitudinally forward within said catheter toward the distal end thereof and around said cam section device and back through the center section of said catheter toward the proximal end of said catheter, wherein a loop of said suture material remains beyond the distal end of said catheter subsequent to the deployment of said suture needle.

6. The medical probe device of claim 5 further including a second suture needle attached to the other end of said suture material, wherein the suture material and the second needle is removable from said catheter via said slot.

7. The medical probe device of claim 6 wherein said suture needle is deployed upon distal movement of said cam section device within said catheter.

8. A medical probe device comprising:
   a hollow catheter having a plurality of needle apertures in the side thereof for directing a plurality of suture needles outward through said needle apertures and through adjacent tissue;
   a suture needle positioned in at least one of said apertures; and
   a deployment apparatus for deploying said suture needles outward through said apertures, said deployment apparatus comprising a wedge segment cylinder device within said catheter, said wedge segment cylinder device comprising a plurality of wedge segment devices within said hollow catheter for urging said suture needle out of said needle aperture upon activation of said deployment apparatus.

9. The medical probe device of claim 8 wherein said wedge segment cylinder device comprises a plurality of wedge segment devices positioned in a cylinder shape and radially within said catheter, each of said wedge segment devices comprising a cam segment device and cam section device combinations.

10. The medical probe device of claim 9 wherein said cam segment device and said cam section devices are generally of complementary cam shapes such that in one position, said cam segment device and said cam section devices are substantially in a mating configuration.

11. The medical probe device of claim 10 wherein said cam segment devices are positioned for longitudinal movement thereof in said catheter, each of said cam segment devices having at least one cam surface.

12. The medical probe device of claim 11 wherein said cam surfaces of said cam segment device contacts said suture needles upon activation, said cam surfaces operating to urge said needles outward of said needle apertures upon longitudinal movement of said cam segment device.

13. The medical probe device of claim 12 wherein said suture needles are curved such that said curve approximates that of said cam surface of said cam segment device, said needles riding in the space defined by the space between said cam segment device and said cam section devices prior to activation of said deployment apparatus, and said needles riding up on said cam surface and outward of said needle apertures upon said longitudinal movement of said cam segment device.

14. The medical probe device of claim 13 wherein each of said suture needles have a distal end and a proximal end, said distal end having a sharp tip and moved outward of said needle aperture, and said proximal end being attached to suture material.

15. The medical probe device of claim 14 further including a plurality of slots in said side of said catheter running from said needle apertures to the distal end of said catheter, said slots allowing the removal of said suture material from said catheter subsequent to deployment of said suture needles.

16. The medical probe device of claim 15 wherein said wedge segment devices are selectively activated to individually deploy said suture needles.

17. The medical probe device of claim 16, wherein said suture needles are positioned within said catheter with the proximal ends of said suture needles facing toward the distal end of said catheter, the suture material attached to each of said suture needles being positioned longitudinally forward within said catheter toward the distal end thereof and around said wedge segment device and back through the center section of said catheter toward the proximal end thereof, wherein a loop of said suture material remains beyond the distal end of said catheter subsequent to the deployment of said suture needles.

18. The medical probe device of claim 17 further including a plurality of second suture needles attached to the other end of each of said suture material, wherein the suture material and the second needles are removable from said catheter via said slots.

19. The medical probe device of claim 18 wherein the cam section devices are fixedly attached within said catheter.

20. The medical probe device of claim 19 wherein said suture needles are deployed upon distal movement of said cam segment device within said catheter.

21. The medical probe device of claim 19 wherein said suture needles are deployed upon proximal movement of said cam segment device within said catheter.

22. A medical probe device for assisting in joining together two or more body parts comprising:
- a hollow catheter having a plurality of needle apertures in a side thereof for directing suture needles outward through said needle apertures and through adjacent tissue;
- a deployment apparatus for deploying each suture needle outward through said needle apertures, said deployment apparatus comprising individual cam sections within said hollow catheter for urging each suture needle out of said needle aperture upon deployment thereof, each of said cam sections having at least one cam surface and being positioned for longitudinal movement thereof in said catheter, wherein said cam surface contacts said suture needle upon activation, said cam surface operating to urge said needle outward of said needle aperture upon longitudinal movement of said cam section,
- a suture needle positioned in each of said apertures, each said suture needle being curved such that said curve approximates that of the curve of the cam surface of said cam sections, each said needle riding in the space defined by said cam surface prior to activation by said deployment apparatus, and said needle riding up on said cam surface and outward of said needle aperture upon said longitudinal movement of said cam sections, each said suture needle having a distal end and a proximal end, said distal end having a sharp tip and moved outward of said needle aperture, and said proximal end being attached to suture material; and
- a plurality of slots in the side of said catheter running from each said needle aperture to the distal end of said catheter, said slots allowing the removal of said suture material from said catheter subsequent to deployment of said suture needle, wherein said suture needle is positioned within said catheter with the proximal end of said suture needle facing toward the distal end of said catheter, the suture material attached to said needle being positioned longitudinally forward within said catheter toward the distal end thereof and around said cam section and back through the center section of said catheter toward the proximal end of said catheter, wherein a loop of said suture material remains beyond the distal end of said catheter subsequent to the deployment of said suture needle.

23. The medical probe device of claim 22 further including a second suture needle attached to the other end of said suture material, wherein the suture material and the second needle is removable from said catheter via said slot.

24. The medical probe device of claim 23 wherein said suture needle is deployed upon distal movement of said cam section within said catheter.

25. The medical probe device of claim 24 wherein said suture needle is deployed upon proximal movement of said cam section within said catheter.

26. A medical probe device for assisting in the joining together of two or more hollow body parts comprising:
- a hollow catheter having a plurality of axial lumens running from the proximal end of said catheter to a position adjacent the distal end of said catheter, each of said lumens curving at the distal ends thereof to exit the catheter in an annular ring of apertures;
- a sharpened suture in each of said lumens, said sharpened sutures comprising suture material with a distal end and a proximal end;
- a deployment slider for each of said sutures and attached thereto and positioned at the proximal end of said catheter for selectively deploying each of said sharpened sutures out of said axial lumens via said apertures into surrounding tissue; and
- a marker band distally forward of said annular ring of apertures for accurately positioning of said catheter within the hollow body part.

27. The medical probe device of claim 26 further including:
- an annular elastic balloon positioned proximally rearwardly of said annular ring of apertures to stabilize said catheter within said hollow body part upon inflation of said balloon; and
- a balloon inflation lumen in said catheter parallel to said plurality of axial lumens coupled to said balloon to provide a path for inflation material to said balloon.

28. The medical probe device of claim 27 further including:

a traction handle emanating from the distal end of said catheter to aid in inserting and positioning said catheter within said hollow body part.

29. The medical probe device of claim 28 further including:

a gripping handle at the proximal end of said catheter of a larger overall diameter of said catheter for firm grasping by an operator, said gripping handle comprising said deployment sliders in an annular arrangement about the exterior of said handle, each of said deployment sliders being mounted in an axial guide path for longitudinal movement therein to deploy or withdraw said sharpened sutures.

30. The medical probe device of claim 29 wherein said sharpened suture comprises a suture material having a sharp point thereon at the distal end thereof.

31. The medical probe device of claim 29 wherein said sharpened suture comprises a needle with a sharp end and a proximal end, and suture material attached to the proximal end of said needle.

* * * * *